United States Patent
Buckley et al.

(10) Patent No.: US 7,969,576 B1
(45) Date of Patent: Jun. 28, 2011

(54) OPTICAL SENSING BASED ON WAVELENGTH MODULATION SPECTROSCOPY

(75) Inventors: Steven G. Buckley, Redmond, WA (US); Mohammadreza Gharavi, Tehran (IR); Marco Borchers, Berlin (DE)

(73) Assignee: The Regents of the University of California, Oakland, CA (US)

( * ) Notice: Subject to any disclaimer, the term of this patent is extended or adjusted under 35 U.S.C. 154(b) by 595 days.

(21) Appl. No.: 12/054,352

(22) Filed: Mar. 24, 2008

Related U.S. Application Data

(60) Provisional application No. 60/896,858, filed on Mar. 23, 2007.

(51) Int. Cl.
*G01N 21/00* (2006.01)
(52) U.S. Cl. .................................................. 356/437
(58) Field of Classification Search .................. None
See application file for complete search history.

(56) References Cited

U.S. PATENT DOCUMENTS

| | | | | |
|---|---|---|---|---|
| 4,684,258 | A * | 8/1987 | Webster | 356/409 |
| 5,026,991 | A * | 6/1991 | Goldstein et al. | 250/343 |
| 6,351,309 | B1 * | 2/2002 | Bomse et al. | 356/437 |
| 6,356,350 | B1 * | 3/2002 | Silver et al. | 356/437 |
| 7,180,595 | B2 * | 2/2007 | Willing et al. | 356/437 |
| 7,217,121 | B2 * | 5/2007 | Thomson et al. | 431/12 |
| 7,251,034 | B2 * | 7/2007 | Kluczynski et al. | 356/437 |
| 7,352,464 | B2 * | 4/2008 | Chen et al. | 356/437 |
| 7,365,352 | B2 * | 4/2008 | Muta et al. | 250/573 |
| 7,508,521 | B2 * | 3/2009 | Liu et al. | 356/437 |
| 7,819,946 | B2 * | 10/2010 | Zhou et al. | 95/90 |
| 2010/0089117 | A1 * | 4/2010 | Liu et al. | 73/1.03 |
| 2010/0242572 | A1 * | 9/2010 | Yu | 73/24.02 |

FOREIGN PATENT DOCUMENTS

JP 05079976 A * 3/1993

OTHER PUBLICATIONS

Angelberger, C. et al., "LES of Chemical and Acoustic Forcing of a Premixed Dump Combuster," Flow, Turbulence and Combustion 65: 205-222 (2000).
Arndt, R. "Analytical line shapes for Lorentzian signals broadened by modulation," J. Appl. Phys. 36(8): 2522-2524 (Aug. 1965).
Bomse, D. et al., "Frequency modulation and wavelength modulation spectroscopes: Comparison of experimental methods using a lead-salt diode laser," Applied Optics, 31(6): 718-731 (1992).
Dore, L., "Using Fast Fourier Transform to compute the line shape of frequency-modulated spectral profiles," J. Mol. Spectrosc. 221: 93-98 (2003).
Gharavi, M. and S. G. Buckley, "A Multiplexed Diode Laser Sensor Based on Wavelength Modulation Spectroscopy for Simultaneous Measurement of Temperature and Concentration of $H_2O$ and $CH_4$," 4th Joint Meeting of the U.S. Sections of the Combustion Institute, Philadelphia, PA, Mar. 20-23, 2005., p. 17, Abstract B10.

(Continued)

*Primary Examiner* — Tarifur Chowdhury
*Assistant Examiner* — Gordon J Stock, Jr.
(74) *Attorney, Agent, or Firm* — Perkins Coie LLP

(57) ABSTRACT

Techniques, apparatus and systems for using Wavelength Modulation Spectroscopy measurements to optically monitor gas media such as gases in gas combustion chambers.

17 Claims, 13 Drawing Sheets

OTHER PUBLICATIONS

Gharavi, M. and S. G. Buckley, "Diode laser absorption spectroscopy measurement of linestrengths and pressure broadening coefficients of the methane $2v_3$ band at elevated temperatures," J. Molecular Spectroscopy, 229: p. 78-88 (2005).

Gharavi, M. and S. G. Buckley, "Single diode laser sensor for wide-range $H_2O$ Temperature measurements," Applied Spectroscopy. 58(4): 468-473 (2004).

Gharavi, M. et al., "Tunable Diode Laser Measurements of Equivalence-Ratio Fluctuations for Premixed Gas-Turbine Applications," 5th U.S. Combustion Institute Meeting 2007, San Diego, California, Mar. 25-28, 2007, Paper E08, pp. 2016-2025.

Girard, J. W., et al., "Use of an Extractive Laser Probe for Time-Resolved Mixture Fractions Measurements in a 9 ATM Gas Turbine Fuel Injector," Presented at the International Gas Turbine & Aeroengine Congress & Exhibition, New Orleans, LA, Jun. 4-7, 2001, 2001-GT-372, pp. 1-8.

Ibrahim, Z. M. et al., "A Study of Combustion-Driven Acoustic Instabilities in Premixed Gas-Turbines Using an Acoustic Energy Framework," 5th U.S. Combustion Meeting. 2007. San Diego, California, Mar. 25-28, 2008, Paper E07, pp. 2006-2015.

Janus, M.C. et al., "Effects of Ambient Conditions and Fuel Composition on Combustion Stability," presented at 1997 American Society of Mechanical Engineers (ASME)/International Gas Turbine Institute (IGTI) Turbo Expo Meeting, Orlando. Florida, Jun. 2-5, 1997, paper DOE/FETC/C-97/7283, 13 pages.

Kluczynski, P. and O. Axner, "Theoretical description based on Fourier analysis of wavelength-modulation spectrometry in terms of analytical and background signals," Appl. Opt. 38(27): 5803-5815 (1999).

Kluczynski, P. et al., "Background signals in wavelength modulation spectrometry with frequency-doubled diode-laser light. II. Experiment," Applied Optics 40(6): 794-805 (2001).

Kluczynski, P. et al., "Background signals in wavelength modulation spectrometry with frequency-doubled diode-laser light, I. Theory," Applied Optics 40(6): 783-793 (2001).

Lieuwen, T.C., "Physics of Premixed Combustion-Acoustic Wave Interactions," Chapter 12 in *Combustion Instabilities in Gas Turbine Engines: Operational Experience, Fundamental Mechanisms, and Modeling*, Lieuwen, T. and V. Yang (Eds.), Progress in Astronautics and Aeronautics. vol. 210. 2006, Reston, VA: AIAA, 2006., pp. 315-366.

Lee, J.G. and D.A. Santavicca, "Experimental Diagnostics of Combustion Instabilites," Chapter 16 in *Combustion Instabilities in Gas Turbine Engines: Operational Experience, Fundamental Mechanisms, and Modeling*, Lieuwen, T. and V. Yang (Eds.), Progress in Astronautics and Aeronautics. vol. 210. 2006, Reston, VA: AIAA, 2006., pp. 481-529.

Lieuwen, T. and B. T. Zinn, "The Role of Equivalence Ratio Oscillations in Driving Combustion Instabilities in Low $NO_x$ Gas Turbines," Proceedings of the 27th Symposium (International) on Combustion/The the Combustion Institute, 1998, p. 1809-1816.

Lieuwen, T. and B. T. Zinn, "Theoretical Investigation of Combustion Instability Mechanisms in Lean Premixed Gas Turbines," 36th Aerospace Sciences Meeting & Exhibit, American Institute of Aeronautics and Astronautics, AIAA98-0641, Jan. 12-15, 1998., Reno, Nevada, pp. 1-14.

Lieuwen, T. et al., "A Mechanism of Combustion Instability in Lean Premixed Gas Turbine Combustors," Journal of Engineering for Gas Turbines and Power (Transactions of the ASME) 123(1): 182-189 (2001).

Philippe, L. C. and R. K. Hanson, "Laser diode wavelength-modulation spectroscopy for simultaneous measurement of temperature, pressure, and velocity in shock-heated oxygen flows," Applied Optics, 32(30): p. 6090-6103 (Oct. 20, 1993).

Reid, J. and D. Labrie, Second-harmonic detection with a tunable diode laser—comparison of experiment and theory. Applied Physics B, No. 26: p. 203-210 (1981).

Richards, G. A. et al., "A Test Device for Premixed Gas Turbine Combustion Oscillations," Journal of Engineering for Gas Turbines & Power (Transactions of the ASME) 119: 776-782 (Oct. 1997).

Rothman, L.S. et al. "The HITRAN 2004 molecular spectroscopic database," Journal of Quantitative Spectroscopy & Radiative Transfer 96: 139-204 (2005).

Schilt, S. et al., "Wavelength modulation spectroscopy: combined frequency and intensity modulation," Applied Optics, 42(33): 6728-6738 (2003).

Silver, J.A. Frequency-modulation spectroscopy for trace species detection: theory and comparison among experimental methods, Applied Optics, No. 31:6 p. 707-717 (1992).

Wahlquist, H., "Modulation broadening of unsaturated lorentzian lines," J. Chem. Phys. 35: 1708-1710 (1961).

Wilson, G. V. H., "Modulation Broadening of NMR and ESR Line Shapes," Journal of Applied Physics 34: 3276-3285 (1963).

Zimmer, L. and S. Tachibana, "Laser induced plasma spectroscopy for local equivalence ratio measurements in an oscillating combustion environment," Proceedings of the Combustion Institute, 31: 737-745 (2007).

* cited by examiner

OPTICAL SENSING BASED ON WAVELENGTH MODULATION SPECTROSCOPY

PRIORITY CLAIM AND RELATED PATENT APPLICATION

This application claims the benefit of U.S. Provisional Application No. 60/896,858 entitled "Optical Sensing Based on Wavelength Modulation Spectroscopy" and filed on Mar. 23, 2007, which is incorporated by reference as part of the specification of this application.

FEDERALLY SPONSORED RESEARCH OR DEVELOPMENT

This invention was made with government support under Grant No. DE-FG26-04NT42172 awarded by the Department of Energy. The government has certain rights in the invention.

BACKGROUND

This specification relates to systems, apparatus and techniques for optical sensing in various applications.

Tunable light sources can be used to measure concentrations of molecules in gaseous or other media by absorption spectroscopy measurements. Examples of such tunable light sources include tunable lasers, e.g., tunable diode lasers (TDLs), and other near- and mid-infrared optical sources. Absorption spectroscopy allows measurements of gas concentration using the well-known Beer-Lambert law, which relates the amount of light absorbed due to a transition corresponding to a particular energy at a wavelength of light to the product of the concentration, the optical path length, and the wavelength-dependent absorption coefficient of the absorbing species. The specific wavelength or wavelengths probed correspond to particular energies associated with quantum-mechanical transitions in the molecule being measured.

SUMMARY

This application includes examples of techniques, apparatus and systems for using Wavelength Modulation Spectroscopy measurements to optically monitor gas media such as gases in gas combustion chambers. In one aspect, a method for optically sensing a gas medium based on the Wavelength Modulation Spectroscopy is described to include modulating a laser wavelength of a tunable laser at a modulation frequency to produce a wavelength-modulated laser beam with a laser frequency range including an absorption band of molecules of a molecular species in the gas medium; directing the wavelength-modulated laser beam that transmits through the gas medium; measuring a transmission of the wavelength-modulated laser beam through the gas medium to obtain measurements of at least one signal at a harmonic frequency of the modulation frequency at different modulation depths in modulating the laser wavelength; and processing the measurements of the at least one signal at the harmonic frequency of the modulation frequency at different modulation depths to obtain a total broadening of absorption spectrum of the molecular species in the gas medium.

In another aspect, a method for performing Wavelength Modulation Spectroscopy measurements is described to include varying a modulation depth in modulating a laser wavelength of a laser used in the Wavelength Modulation Spectroscopy for measuring a gas medium to obtain measurements; and obtaining a total pressure broadening from the obtained measurements without prior knowledge of individual pressure broadening coefficients and gas composition.

In another aspect, a method for optically measuring a gas medium based on the Wavelength Modulation Spectroscopy is described to include directing a laser beam from a wavelength-modulated tunable diode laser through the gas medium; and measuring two different harmonic signals which have different responses to a total pressure in the gas medium to obtain both a gas concentration and a total pressure in the gas medium.

In another aspect, a method for optically measuring a gas medium based on the Wavelength Modulation Spectroscopy is described to include directing a first laser beam from a first wavelength-modulated tunable diode laser through the gas medium and a second laser beam from a second wavelength-modulated tunable diode laser through the gas medium, wherein the first wavelength-modulated tunable diode laser and the second wavelength-modulated tunable diode laser are modulated at respective modulation frequencies; operating the first and the second tunable diode lasers differently with respect to a respective optimum modulation depth; and measuring a harmonic signal of the modulation frequency from the first laser beam and a second harmonic signal at a harmonic frequency of the second laser beam to obtain both a gas concentration and a total pressure in the gas medium.

In yet another aspect, a gas turbine system is described to include a gas turbine having a premixing gas chamber; a first input port to input air into the premixing gas chamber; a second input port to input a gas fuel into the premixing gas chamber to mix with the air; a wavelength modulation spectroscopy (WMS) optical monitoring device having at least one tunable laser to produce a wavelength-modulated laser beam and to direct the laser beam through at least a portion within the premixing gas chamber to interact with a mixture of the gas fuel and the air; and an optical detector to receive an optical transmission of the laser beam; a WMS processing device that processes an output of the optical detector to extract at least one signal at a harmonic frequency of the modulation frequency at different modulation depths; and a turbine control mechanism in communication with the WDM processing device and operable to control the gas fuel and the air input into the premixing gas chamber based on information in the at least one signal at the harmonic frequency of the modulation frequency.

These and other aspects, examples and implementations of techniques, apparatus and systems for using Wavelength Modulation Spectroscopy measurements to optically monitor gas media are described in detail in the drawings, the description and the claims.

DETAILED DESCRIPTION

Figure 1A:
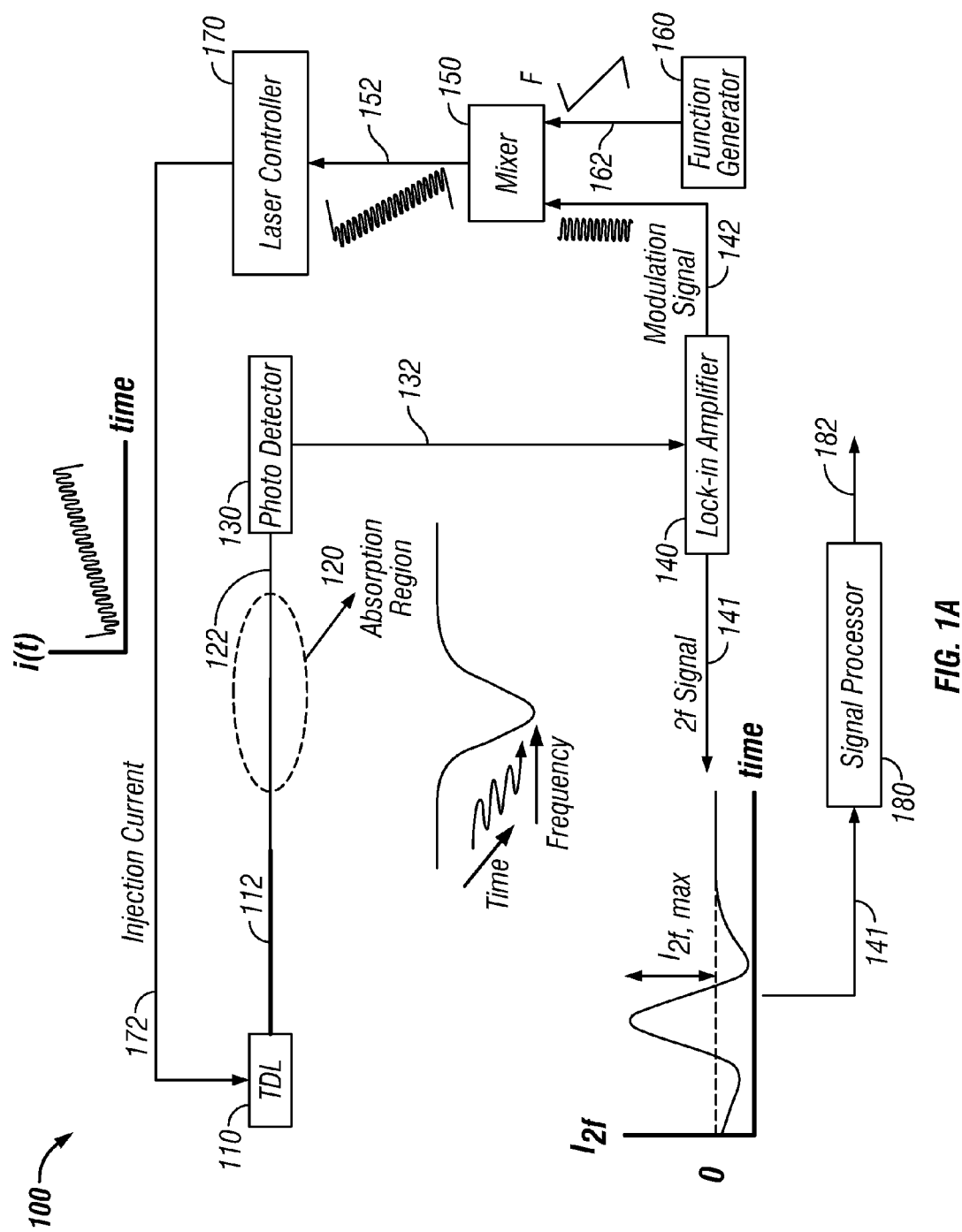
FIG. 1A shows an example of a wavelength modulation spectroscopy (WMS) measurement system using a tunable diode laser, where a lock-in amplifier function can be accomplished in software or hardware.

Optical sensing based on absorption spectroscopy can face various technical difficulties in practical implementations. For example, while the energy associated with an optical transition in principle can be a nearly exact quantity, the actual quantum mechanical energy measured can be uncertain, or spectrally "broadened", due to various factors. One of such factors, for example, is collisions of molecules with the absorbing species during the act of absorption. This collision-induced broadening is known as "collisional broadening" or "pressure broadening." Another factor is that molecules may be moving toward or away from the optical detector during light absorption and this motion of the light absorbing molecules can cause "Doppler broadening" of the linewidth of the optical signal detected by the optical detector. In some samples under measurement, these two effects can be comparable in magnitude under elevated temperatures at the atmospheric pressure. The total broadening is important for quantification of the signal parameters in the detected absorption signal.

Quantification of absorption spectroscopy via the Beer-Lambert law involves optical integration of the absorption peak, which has a variable width, before the law is applied in the signal processing. At higher pressures and temperatures, this optical integration of the absorption peak can be problematic because the width of the absorption peak can be more than the tuning width of the laser source. In addition, the absorption spectroscopy is the detection of a small dip or reduction in optical absorption in a large optical signal which is the power level of the probe beam from the laser or other light source and hence the sensitivity in many applications can be limited due to presence of noise from many sources. Therefore, it is desirable to increase the sensitivity in signal detection for absorption spectroscopy in order to achieve accurate measurements.

Wavelength modulation spectroscopy (WMS) is a known method of modulating a laser and detecting the associated optical absorption with a frequency-selective filter (such as a lock-in amplifier). A WMS technique that is suitable for implementing the present techniques and systems can be configured to have a modulation frequency selected from a range of different modulation frequencies and is not limited to a particular frequency range of modulation. The systems, apparatus and techniques described in this specification can be used to exploit spectroscopic properties of odd- and even-numbered harmonics of the modulation frequency (first harmonic, "1f", second harmonic, "2f", fourth harmonic, "4f", etc.) in wavelength modulation spectroscopy to achieve desired measurements for various optical sensing applications, including molecular concentrations and pressure levels in gaseous media such as gases in a combustion chamber, in a turbine, or in other systems. The use of harmonics of the modulation frequency described here can significantly reduce or minimize background noise in signal detection and to create spectra with a near-zero baseline. In some implementation, the present WMS techniques can be used to improve the detection sensitivity by two orders of magnitude or more over other direct absorption quantification based on the Beer-Lambert law. The analysis associated with the quantification based on the use of harmonics of the modulation frequency can also be used to allow a selected portion of the line shape to be measured. This ability can be used to avoid the technical difficulty in measuring the target gas medium with a linewidth greater than the tuning range of the optical source to provide model-based quantification of the concentration in a wide range of conditions.

FIG. 1A shows an example of a WMS measurement system 100. A tunable diode laser 110 is provided to produce a laser beam 112 and the laser wavelength is modulated at a modulation frequency under a control by a driving injection current 172 that is injected into the TDL 110. A laser controller 170 is provided to generate the driving injection current 172. The driving current 172 is modulated at a modulation frequency f to modulate the laser wavelength or frequency. The wavelength-modulated laser beam 112 is directed through an absorption region 120 (e.g., a gas chamber) that contains a target sample to be measured and the optically transmitted light 122 out of the absorption region 120 is directed into an optical detector 130. A signal mixer 150 is used to mix the modulation signal 142 and a sweep signal 162 at a sweeping frequency F from a sweep signal generator 160. The output signal 152 from the mixer 150 is fed into the laser controller 170 which produces the injection current 172 that carries the modulation signal 142 at a harmonic frequency and the sweep signal 162.

The detector output 132 of the detector 130 can be processed by a signal processing software to extract the harmonic signals 141 such as 2f and 4f signals to obtain the desired measurement such as a molecular concentration or the gas pressure of the gas in the absorption region 120. Alternatively, one or more lock-in amplifiers 140 can be used to extract the desired one or more harmonic signals 142 as the modulation signal. In the example in FIG. 1A, one lock-in amplifier 140 is used to extract the 2f signal. Other software- or hardware-based methods of lock-in detection could be equivalently used. A signal processor 180, e.g., a computer, can be used to process the 2f signal 141 and to obtain the total line broadening 182 from the measured harmonic signals.

Figure 1B:
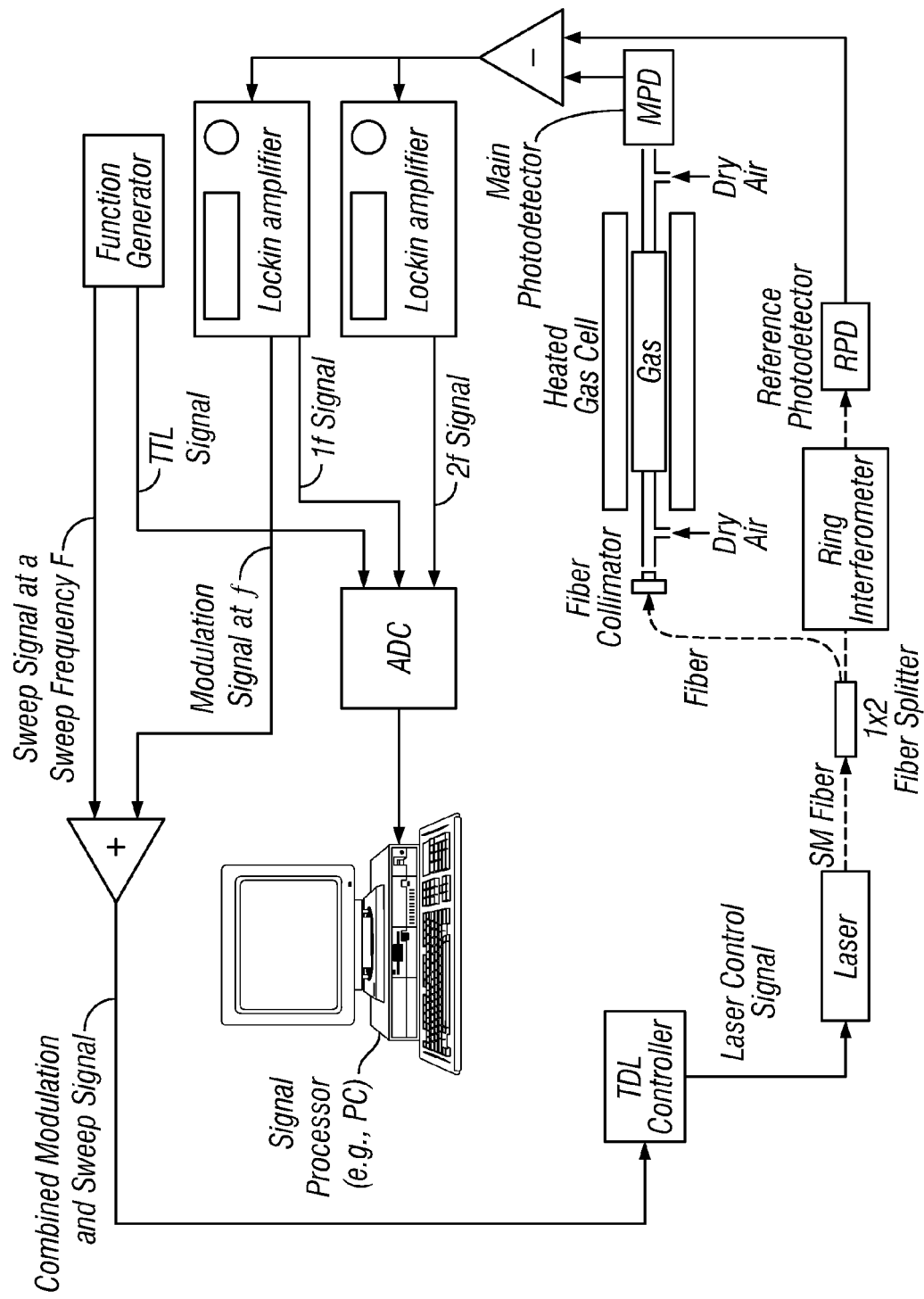
FIG. 1B shows another example of a wavelength modulation spectroscopy (WMS) measurement system.

FIG. 1B shows another example of a WMS measurement system that has been used in practice. The TDL 100 in this example is a distributed feedback (DFB) diode laser (e.g., operating around 1477 nm to measure $H_2O$) is modulated with a 10 kHz sine modulation wave while being slowly tuned by a 10 Hz sweep signal from a function generator. The output of the laser split into a reference beam and a probe laser beam which is passed through a static gas cell containing a gas mixture of $H_2O$ and bath gases at known pressure and temperature. The attenuated probe laser beam is measured by a main photodetector (e.g., a Germanium photodetector). To reduce the laser intensity noise and also remove the second harmonic background, a portion of the laser beam is split off as the probe beam and is directed into a reference photodetector. The reference photodetector produces a reference signal. The reference signal and the main detector signal are subtracted at a subtraction circuit (e.g., a differential amplifier) so that they cancel each other everywhere beyond the absorption region.

The subtracted signal is sent to two lock-in amplifiers where the first and second harmonics of the subtracted signal are measured. The amplitude of the first harmonic signal at the absorption line center or in regions with no absorption is proportional to the laser intensity, and therefore is used for normalization of the second harmonic signal with respect to the laser power impinging on the photodetector. The outputs from the lock-in amplifiers are stored on a desktop computer and post-processed. To avoid absorption of atmospheric water vapor along optical path outside the static cell, this region is purged with dry air. For conversion of the data as a function of time to its corresponding optical frequency, a ring interferometer with a free spectral range (FSR) of 0.02269 $cm^{-1}$ can be used. The reference signal is sent to a ring interferometer, while the modulation signal is turned off. The signal at the output of the ring interferometer is detected by the reference photodetector and then is stored in the computer as the signal processor. The fringes in the signal are used to determine the relative frequency during the sweep.

Figure 2:
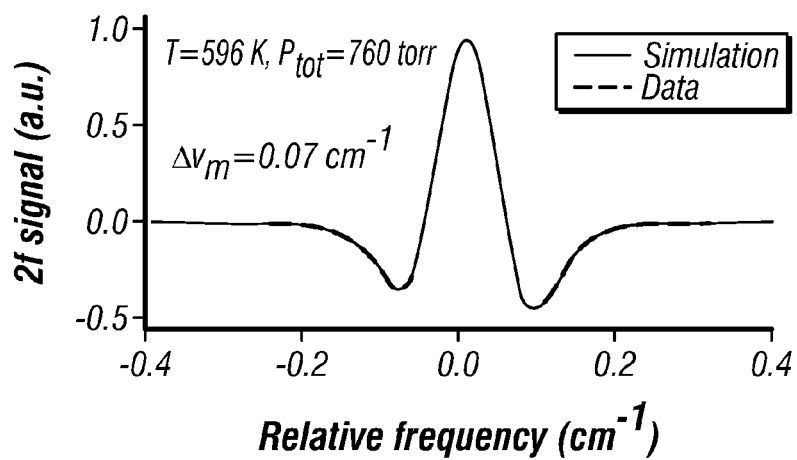
FIG. 2 shows spectral measurements of methane at a temperature of 596K and under a pressure of 760 torr and a spectral curve in a solid line based on a line broadening model.

The systems in FIGS. 1A and 1B for WMS quantification can be configured to provide speedy quantification of molecular concentrations and pressures for various applications, including measurements in unknown environments, without the need for pre-determined data on line broadening information, and to provide separation of concentration and pressure fluctuations by measuring and processing different harmonic signals such as 2f and 4f signals to provide efficient optical sensing. Some other WMS methods require laborious measurements of the broadening coefficients to obtain proper quantification and this approach can be time-consuming, e.g., it may take weeks or months for each molecular transition to be quantified. Based on the known properties of the broadening, a spectral broadening model and the theory can be in good agreement. FIG. 2 shows spectral measurements of methane at a temperature of 596K and under a pressure of 760 torr and a spectral curve in a solid line based on a line broadening model. The overlap between the model simulation and measurement data is sufficiently close to allow measurements of concentrations with an accuracy better than ±1%.

The present techniques can be used to directly measure the broadening during measurements using the instrument and the measurement can be simultaneously optimized. The amplitude of the wavelength modulation of the diode laser 110 can be varied rapidly during measurement. The absorption spectral lineshape in a gas medium tends to have a Voigt spectral profile but in the low and high pressure limits the lineshapes can be approximated by Gaussian and Lorentzian lineshapes, respectively. The second harmonic absorption amplitude peaks at a wavelength modulation depth equal to 2.2 times the broadened line width. Other harmonics have known peaks at different modulation depths with respect to the line width. See, for example, Reid, J. and D. Labrie, *Second-harmonic detection with a tunable diode laser-comparison of experiment and theory*. Applied Physics B, No. 26: p. 203-210 (1981). Under the condition that the concentration of the species under measurement over this period is steady, the total broadening in the system can be measured by varying the amplitudes of the laser beam(s) modulation and measurement of the harmonic signal(s) intensity, and the concentration of the species can be quantified from the measured total line broadening.

Figure 3:
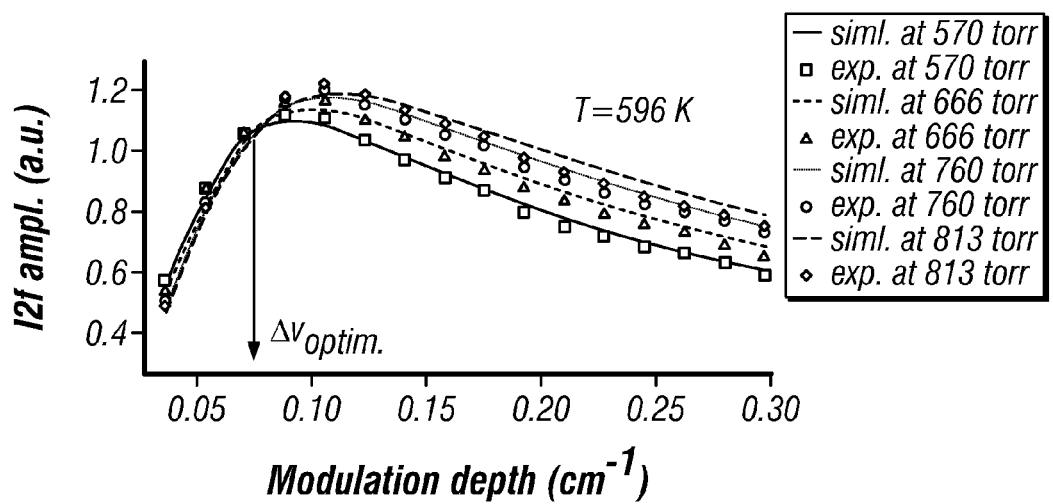
FIG. 3 shows data for variations of the 2f amplitude versus modulation depth at different pressures for a fixed mixture of 0.31% CH4 and 99.69% air at a temperature of 596 K.

FIG. 3 shows measurements of amplitudes of the 2f signal as a function of the modulation depth under a variety of total pressures and at an elevated temperature of 596 K. The data suggests that there is a maximum in the intensity of the 2f absorption signal ("I2f") on the y-axis when the amplitude of modulation ("modulation depth") is varied in experiments. It is possible to predict this variation closely as indicated by solid lines from a theoretical lineshape model. The model can be fitted to the data to derive the total broadening from the measured maximum absorption, taking into account, for instance, Doppler broadening and pressure broadening; other broadening mechanisms could also be considered. This technique can be used to provide speedy determination of the linewidth in WMS and allows the WMS to be used for optical sensing in various sensing applications, in particular those in which the gas mixture and/or the broadening coefficients are unknown.

Notably, the 2f and 4f signals in WMS measurements respond differently to changes in the total pressure depending on the modulation depth. This aspect of the WDM measurements is disclosed in literature, for example, Silver, J. A. *Frequency-modulation spectroscopy for trace species detection: theory and comparison among experimental methods*, Applied Optics, No. 31:6 p. 707-717 (1992). The optimum 2f absorption for a Lorentzian line shape (which is dictated by the effects of temperature and pressure broadening) is at a modulation depth of 2.2 times the broadened linewidth, while the optimum 4f absorption occurs at a different modulation depth equal to 3.9 times the broadened linewidth.

Figure 4:
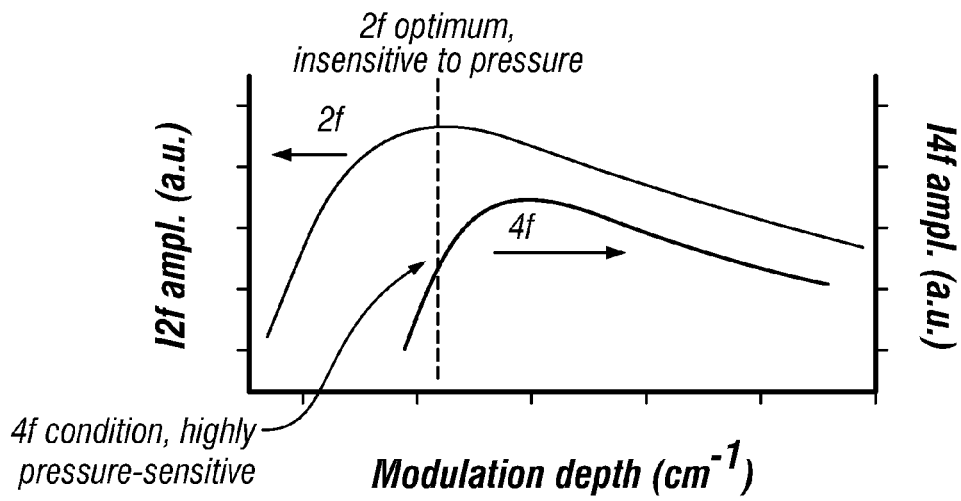
FIG. 4 illustrates an example of simulated amplitudes of 2f and 4f signals in WMS measurements with respect to the modulation depth to show the difference between the 2f and 4f signals.

FIG. 4 illustrates an example of the amplitudes of 2f and 4f signals with respect to the modulation depth to show the above difference between the 2f and 4f signals. Based on this difference, the 2f and 4f signals can be simultaneously measured and processed in WMS to simultaneously measure concentration and pressure fluctuations in a gas medium.

Therefore, when the 2f signal is optimized at its optimized modulation depth and exhibits little variation with the pressure, concentration, or other parameters, the 4f signal is not optimized and thus exhibits measurable variations with the pressure, concentration, or other parameters. Conversely, when the 4f signal is optimized at its optimized modulation depth and exhibits little variation, the 2f signal is not optimized and thus exhibits measurable variations. Other different harmonic signals other than 2f and 4f signals also exhibit similar signal behaviours. Such differences in two or more different harmonic signals in WMS can be used to provide measurements for determining two or more parameters of a gas medium measured by WMS.

Referring to FIG. 3, near the pressure-dependent optimum (e.g. ±0.01 or 0.015 $cm^{-1}$), the total absorption $I_2f$ is essentially constant for the 2f signal. For the 4f signal, however, the modulation exhibits a strong pressure dependence. If the 4f signal were optimized, the 4f signal would have negligible pressure dependence, but the 2f signal would have substantial pressure dependence.

Figure 5A:
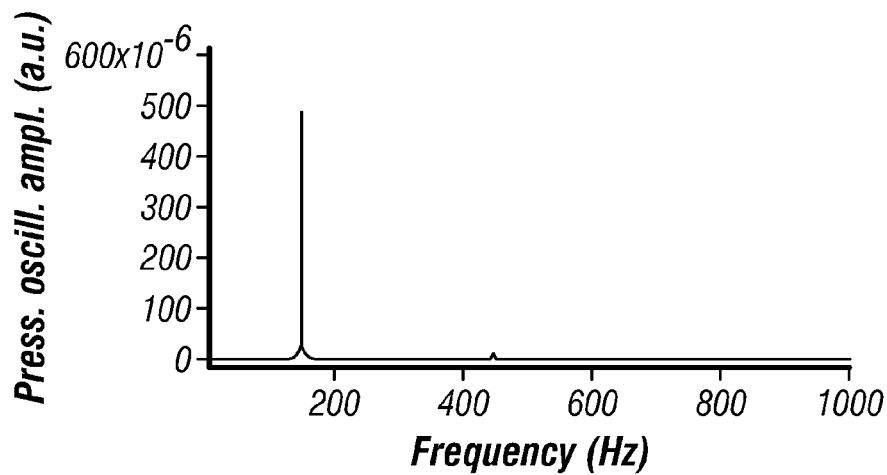
FIGS. 5A, 5B and 5C show measurements obtained from WMS in which the total pressure is modulated using a speaker, and the 2f and 4f absorption signal are measured.
Figure 5B:
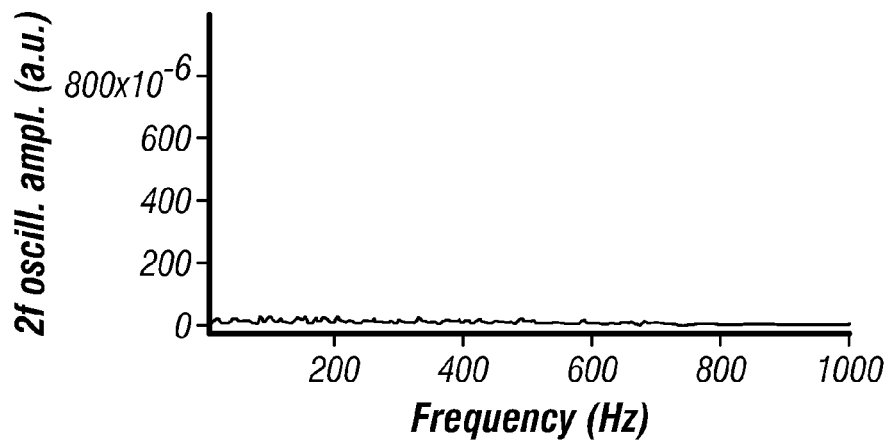
Figure 5C:
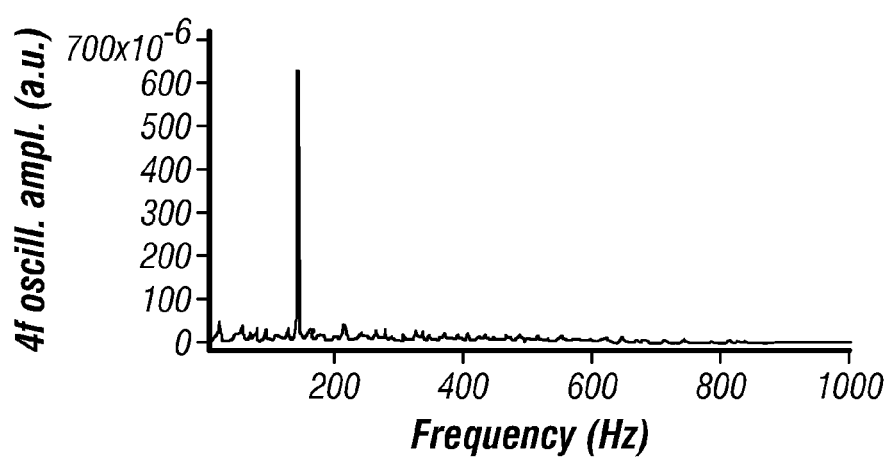

FIGS. 5A, 5B and 5C show measurements obtained from WMS in which the total pressure is modulated using a speaker, and the 2f absorption signal is optimized. FIG. 5A shows the Fourier transformed output of a pressure transducer, which has a strong peak near 160 Hz. The 2f signal is optimized and the Fourier transform of the 2f signal shown in FIG. 5B does not exhibit a significant variation to indicate the pressure modulation. The 4f signal in FIG. 5C varies with the pressure. This differences in 2f and 4f signals can be used in various applications to determine the line broadening and the concentration of a gas in systems such as combustion (e.g. gas turbine, engine, rocket) systems in which a measurement system may be needed to measure and/or distinguish between both gas concentration fluctuations and pressure fluctuations. Two harmonics yield two variables; solution of two equations in two unknowns allows separation of these two potentially confounding variables.

Figure 6:
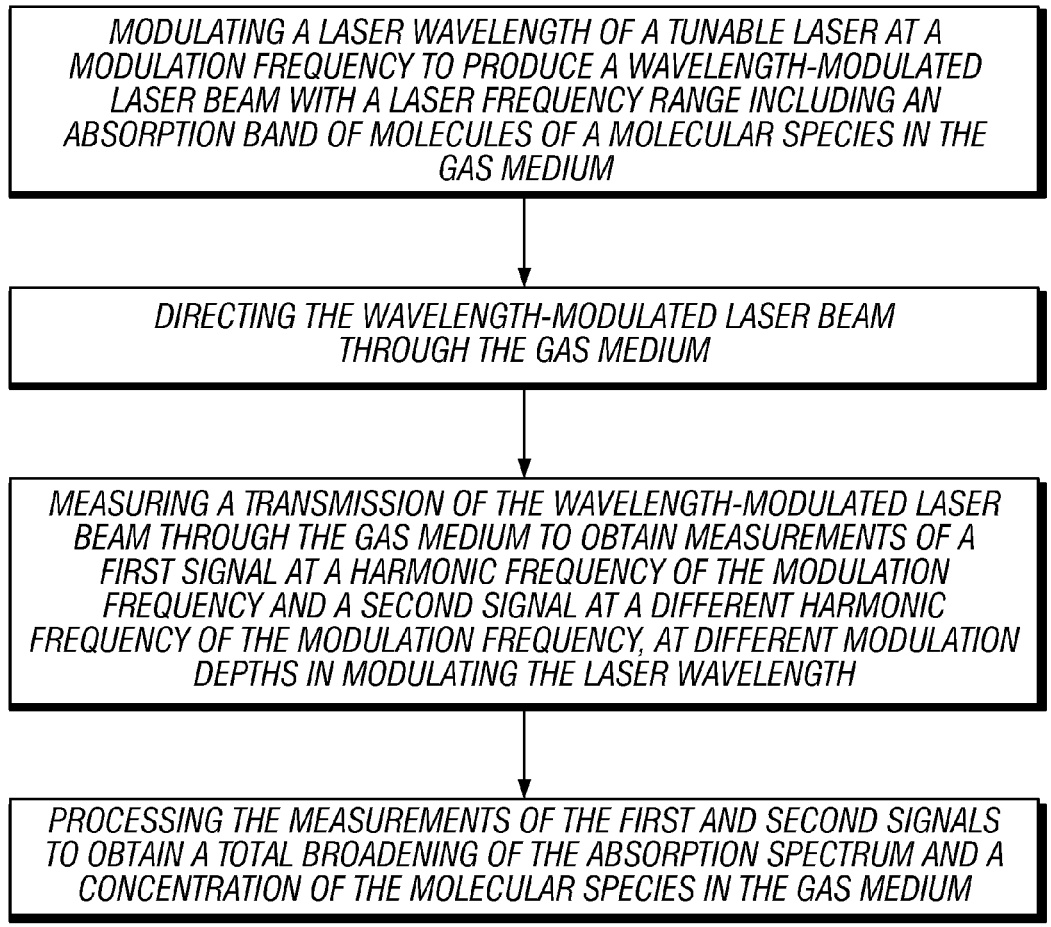
FIG. 6 shows a WMS measurement process based on the response of two different harmonic WMS signals.

FIG. 6 shows a WMS process based on two harmonic signals. This process includes modulating a laser wavelength of a tunable laser at a modulation frequency to produce a wavelength-modulated laser beam with a laser frequency range including an absorption band of molecules of a molecular species in the gas medium; directing the wavelength-modulated laser beam through the gas medium; and measuring a transmission of the wavelength-modulated laser beam through the gas medium to obtain measurements of a first signal at a harmonic frequency of the modulation frequency and a second signal at a different harmonic frequency of the modulation frequency, at different modulation depths in modulating the laser wavelength; and processing the measurements of the first and second signals to obtain a total broadening of the absorption spectrum and a concentration of the molecular species in the gas medium.

Examples for implementing the techniques described above described below based on the fact that the even harmonic components in wavelength modulation spectroscopy (2f, 4f, etc. . . . signals) are dependent on the line-shape which is dependent on the gas pressure and the concentration. An oscillation in either or both of the pressure and the gas concentration can lead to an oscillation in one or more harmonic signals and the measurements of the harmonic signals can detect the line broadening in the gas and the gas concentration.

For example, some WMS systems can use a single tunable laser, such as a diode laser, to perform the WMS measurements. The laser can be modulated at a modulation frequency f, where the 2f and 4f signals of the absorption peak of the measured gas species (such as $CH_4$) are measured simultaneously. The laser modulation depth is set in such a way that the 2f signal is completely independent of the total pressure fluctuation and therefore any measured oscillation in the 2f signal is directly related to the fuel concentration oscillation. Under these conditions a 5% oscillation in the 2f signal would represent the existence of 5% oscillation in fuel concentration (under conditions with low absorbance) even if there were some total pressure fluctuation in the system. Since the 4f signal behaves quite differently from the 2f signal at the selected modulation depth, the 4f signal would strongly depend on pressure and could be used to measure overall pressure fluctuations. In cases in which the system experienced both fuel and pressure oscillation, the information from the 2f and 4f signals could be used to measure the amplitude of each of these oscillations simultaneously.

Figure 7:
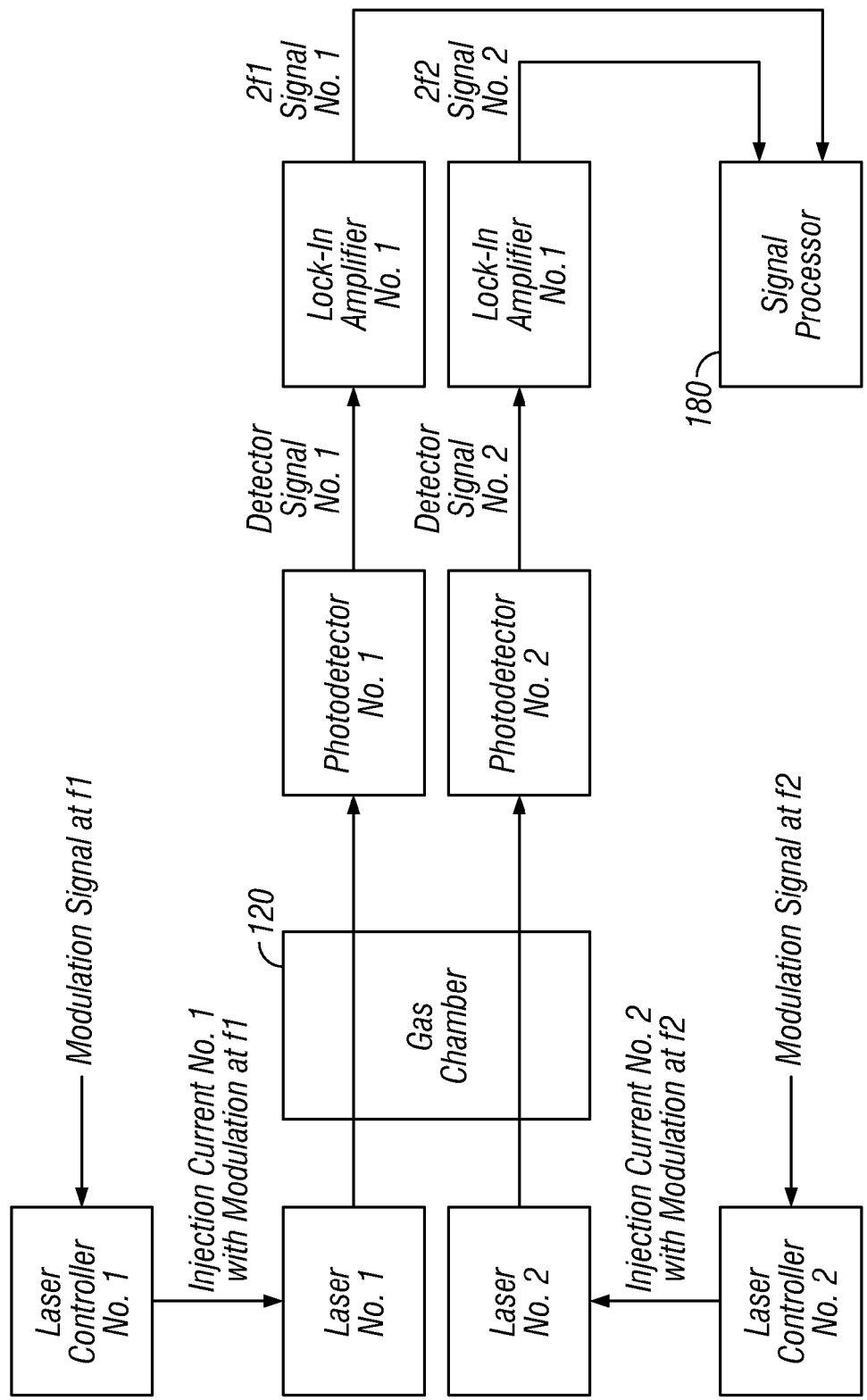
FIG. 7 shows an example of a WDM system with two lasers.

As another example, FIG. 7 shows a WMS system that uses two multiplexed lasers No. 1 and No. 2 that are operated at the same optical frequency corresponding to the gas absorption frequency. Each laser is operated at a different modulation frequency and amplitude. The modulation frequency f1 of the first laser is set in such a way that the 2f1 signal will be independent of pressure fluctuation and therefore is used to directly measure an oscillation in the gas concentration. The second laser is operated at conditions where its 2f2 signal will be most sensitive to pressure (in contrast to the first laser). Therefore, the 2f2 signal from the second laser provides information about fluctuations due to both pressure and gas concentration. Two photodetectors No. 1 and No. 2 are used to receive and detect the two laser beams from the two lasers, respectively. The 2f1 signal and the 2f2 signal are extracted from the two detector signals out of the two photodetectors, respectively. A signal processor 180 is used to process the extracted 2f1 signal and the 2f2 signal to simultaneously measure fluctuations due to pressure and gas concentration. Other even-numbered harmonics (4f, 6f, 8f, etc.) can also be used in this manner as well. While the single laser setup is simple in structure, a higher harmonic signal such as 4f is needed in addition to the 2f signal to simultaneously measure the total line broadening and the concentration. The two-laser system can use two different 2f signals from the two laser probe beams in measurements where the absorption signal is weak and therefore an optimum S/N ratio is sought because the 2f signals are generally more sensitive than higher harmonics such as the 4f signal.

The techniques described above can be used to obtain measurement of the fuel/air ratio, for example, in a gas turbine. Gas turbines are a particular class of high-speed, rotating machinery in which the dynamics and potential control of the air and fuel need to happen on millisecond time scales. Tunable diode lasers, developed by the telecommunications industry and capable of wavelength modulation at GHz rates, are a suitable optical source to perform fast optical measurements and control. Of particular interest is the effect of thermoacoustic instabilities in the main combustion chamber, which can cause pressure pulses. These pressure pulses, also referred to as pressure oscillations, can propagate back into the premixer area ahead of the flame, where the fuel and air mix. It is widely assumed that the influence of thermoacoustic instabilities on the premixer may cause fluctuations in the fuel/air ratio, which would then feed forward into the flame, amplifying the thermoacoustic instability. Therefore, it can be important to measure the concentration of a fuel (such as $CH_4$, a component of natural gas), or a product (such as $CO_2$ or $H_2O$) and the total system pressure simultaneously. The present WMS techniques can be used to measure the fuel concentration, product concentration, or fuel/air ratio in the presence of total pressure fluctuations, and quantify both the gas concentrations and the total pressure fluctuation simultaneously. Such measurements can be useful for mitigation and control of gas turbine oscillations and/or emissions and may be used in real-time monitoring and controlling of a gas turbine. Similar considerations make this an effective measurement method for other gaseous systems where simultaneous temperature and pressure measurements are required, such as manufacturing processes, energy plant processes, and transportation process engines.

Figure 8:
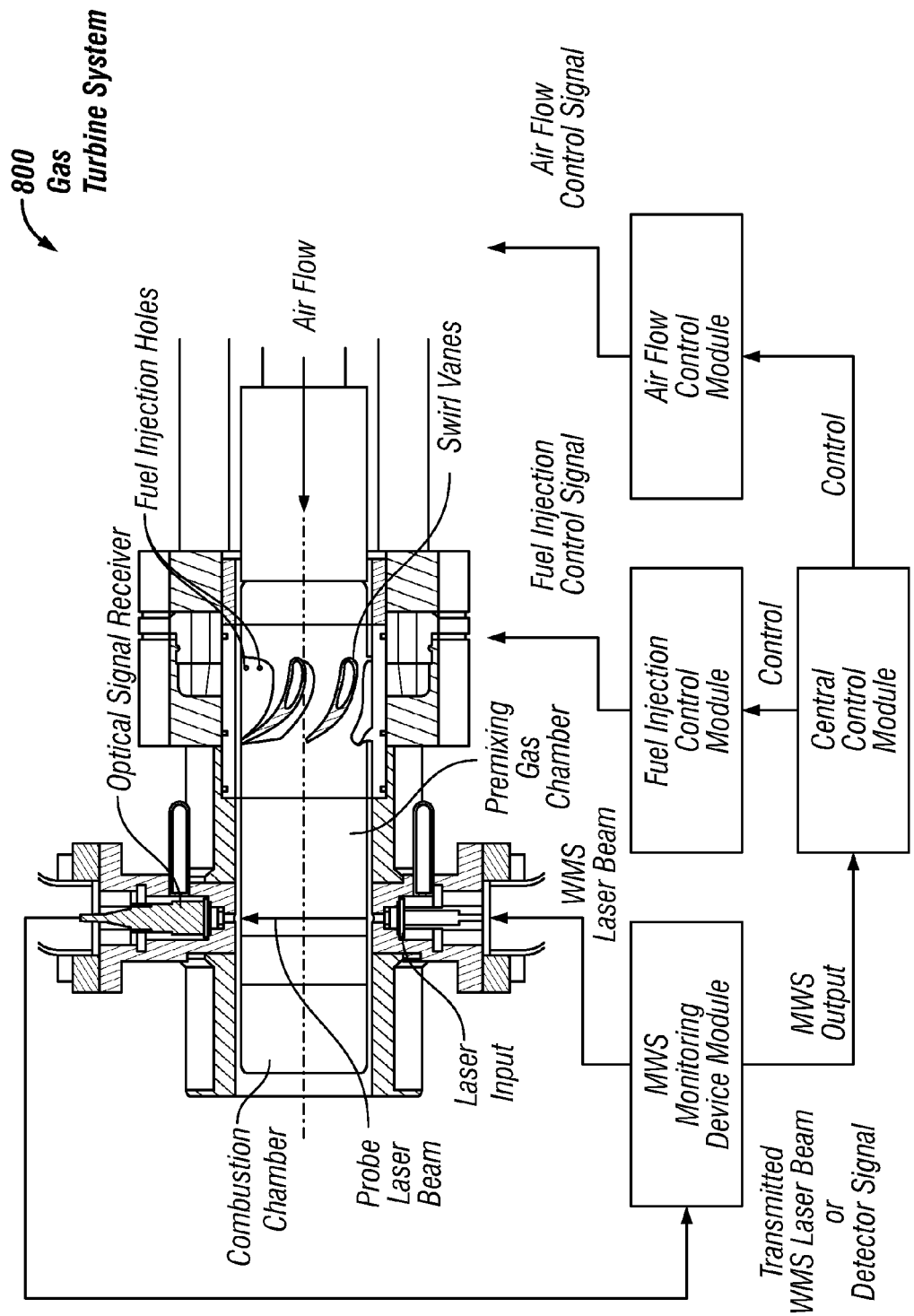
FIG. 8 shows an example of a gas turbine system that incorporates a WMS monitoring module as part of its system control.

FIG. 8 shows an example of a gas turbine system 800 that incorporates a WMS monitoring module as part of its system control. The system 800 includes a gas turbine 801 having a premixing gas chamber where the air and the fuel are mixed with each other. The mixture is injected to the combustion chamber and is ignited to cause combustion. The gas turbine is configured to include a first input port to input air into the premixing gas chamber, a second input port with fuel injection holes to input a gas fuel into the premixing gas chamber to mix with the air. The premixing gas chamber includes a laser input port to receive a laser beam and a signal receiver port to receive the laser beam that enters the premixing gas chamber from the laser input port and transmits through the premixing gas chamber. A wavelength modulation spectroscopy optical monitoring device is provided as part of the gas turbine system 800. The WMS device has at least one tunable laser to produce a wavelength-modulated laser beam and to direct the laser beam through at least a portion within the premixing gas chamber to interact with a mixture of the gas fuel and the air; and an optical detector to receive an optical transmission of the laser beam that is received at the signal receiver port. A WMS processing device is provided in the WMS device to process an output of the optical detector to extract at least one signal at a harmonic frequency of the modulation frequency at different modulation depths.

A turbine central control module is provided as part of the control mechanism to be in communication with the WMS processing device to receive the WMS output from the MWD device. The central control module is operable to control the gas fuel and the air input into the premixing gas chamber based on information in the at least one signal at the harmonic frequency of the modulation frequency. As illustrated, the gas turbine system 800 includes a fuel injection control module that controls the injection of the fuel into the premixing gas chamber and an air flow control module that controls the injection of the air flow into the premixing gas chamber. The central control module commands the fuel injection and air flow control modules which in turn to control the gas fuel and the air input into the premixing gas chamber.

Tests were conducted in a 8"×20" cylindrical combustor using a standard injector for a gas turbine with a power rating of 7.5 MW, where the end barrel was modified to allow optical access along a 4.7 cm path length. The fuel flow rate was varied between 25-45 lbs/hour and the air flow rate was maintained at approximately 0.3 lbs/sec while mapping the pressure oscillations. Pressure oscillations were measured using a Kistler dynamic pressure sensor mounted on a Swagelock-T off of a torch feed line. A torch was used to light the combustor and had a ¼" tube into the base of the chamber. The optical probes, all delivered through optical fibers, were cooled using a nitrogen flow. The optical access was placed as far as possible downstream of the swirl vanes to allow maximum mixing of fuel and air before entering the chamber. This rendered a mixing length of 1" before reaching the laser detection plane.

To measure the harmonic signals of CH4, I2f or I4f, a custom built WMS optical sensor was used. The sensor included a) a fiber-pigtailed DFB laser operating at 1650 nm from OKI, b) a diode laser temperature and current controller from ILX Lightwave, c) a 24-bit dynamic signal acquisition and generation PXI module with 204.8 kS/sec, d) a PXI controller (computer) module, e) a PXI chassis (the PXI modules and chassis are from National Instruments), f) two fiber-pigtailed collimator/couplers for sending to and receiving from the probed gas region, and h) a photodetector with a detection bandwidth of 200 kHz from New Focus. The optical sensor was used to measure the harmonic signals from absorption associated with the R4 manifold of CH4 from a 2v3 band transition. To obtain the maximum response time, the laser frequency was modulated at the center of the absorption feature at a frequency of 5 or 10 kHz, with no sweep tuning applied. Depending on the fuel/air mixture temperature, the laser was operated at the corresponding optimum modulation amplitude to obtain the information related to the equivalence-ratio oscillation. The modulated laser beam, after collimation by a fiber-pigtailed collimator, was passed through the probe region and after being coupled into the receiving optical fiber, is detected by the photodetector. The photodetector signal was acquired by the dynamic signal acquisition module and then was demodulated digitally. The harmonic signals at frequencies of the modulation frequency f, the second harmonic at 2f and the fourth harmonic at 4f of the absorption feature were calculated based on the digital data of the measurements. The measured 2f signal (or 4f signal) was used for measuring the frequency and amplitude of equivalence-ratio oscillation. The acquisition module also acquired a voltage signal from the conventional pressure sensor for measurement of the amplitude and the frequency of the gas pressure oscillation. The Fast Fourier Transformation (FFT) was applied to the measured 2f signal (or 4f signal) and pressure signal, the frequency and amplitude of fuel mole fraction and pressure oscillation were measured in real-time (updating each second). All hardware communications, modulation and demodulation processes (such as signal generation/acquisition, digital lock-in detection, and FFT analysis) were performed and controlled through a LabView™ code developed in-house.

Figure 9:
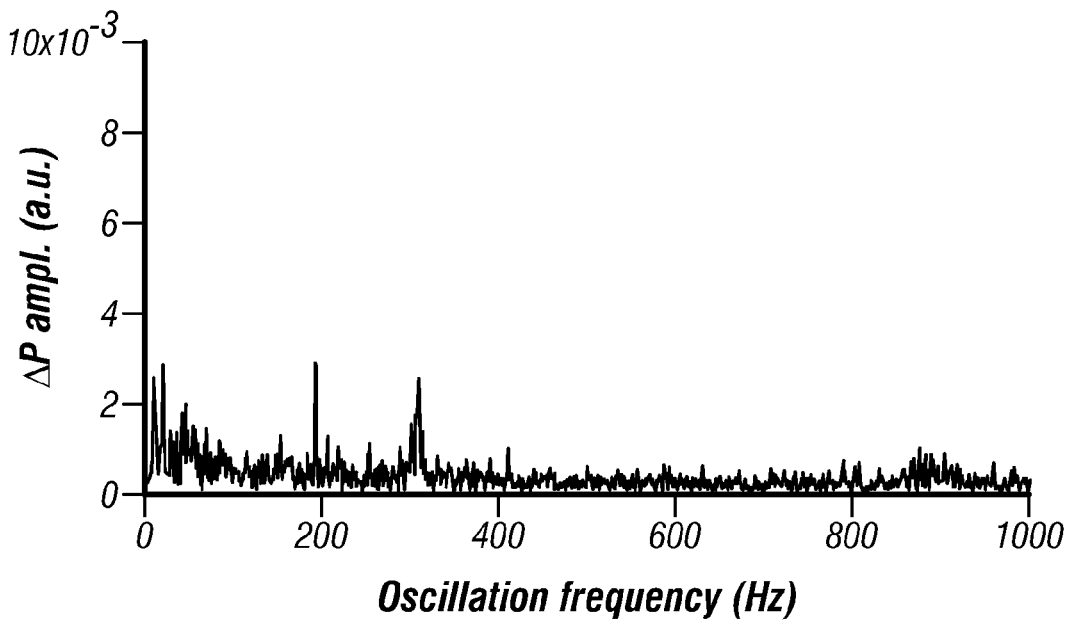
FIG. 9 shows a sample of FFT data obtained in the system in FIG. 8, updated at 1 Hz, from the pressure sensor, on the top, and the optical sensor (on the bottom) when two main oscillation modes were observed.
Figure 9:
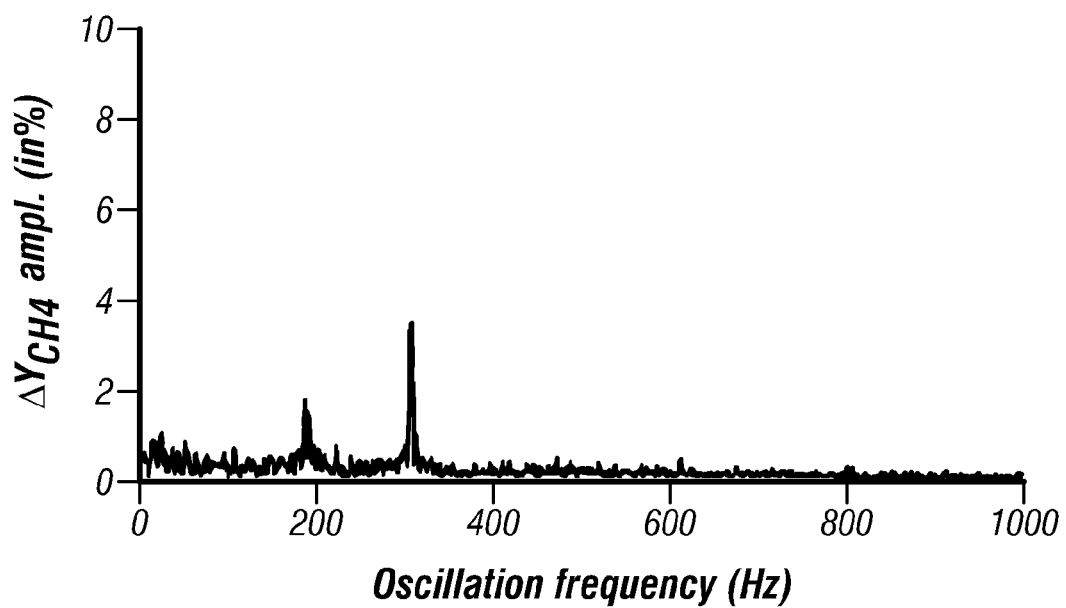
Figure 10:
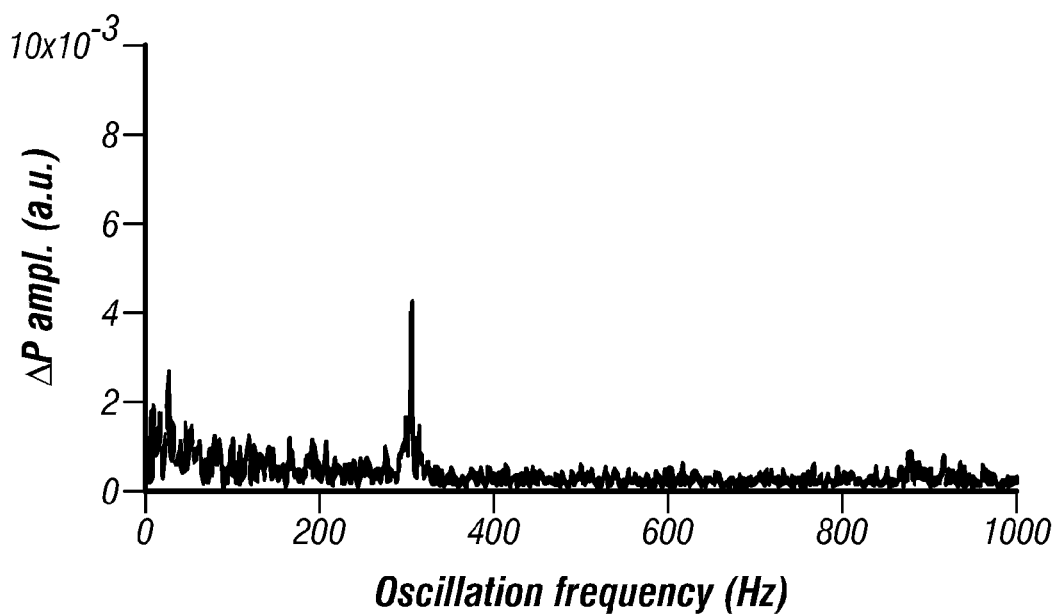
FIG. 10 shows sample of FFT data obtained in the system in FIG. 8 from the pressure sensor, on the top, and optical signal (on the bottom) when only one main oscillation mode was observed.
Figure 10:
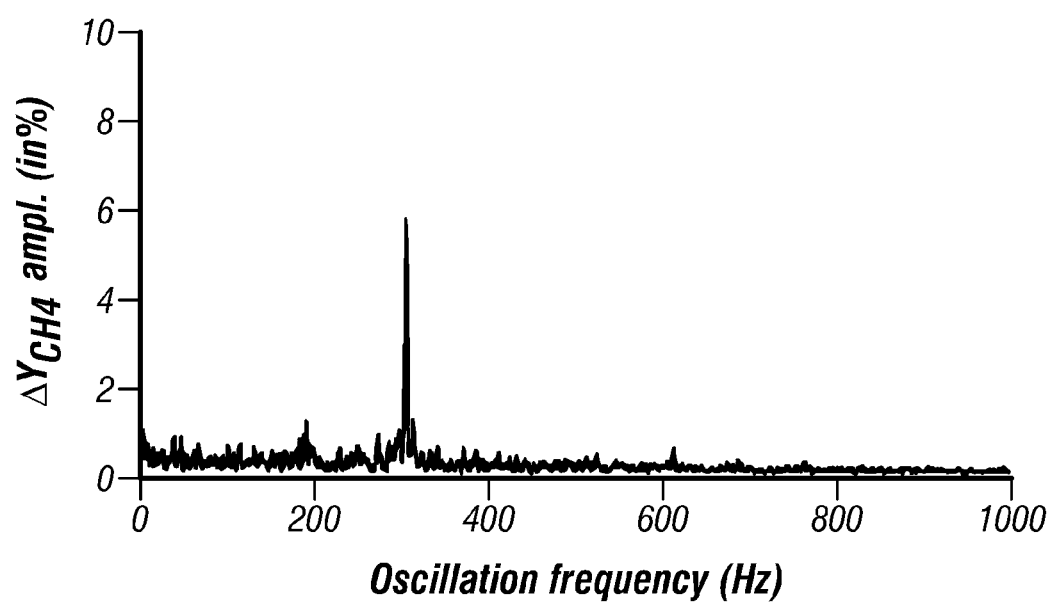

FIGS. 9 and 10 show examples of the oscillation measurements obtained in the system in FIG. 8. FIG. 9 shows a sample of FFT data obtained, updated at 1 Hz, from the pressure sensor, on the top, and the optical sensor (on the bottom) when two main oscillation modes were observed. FIG. 10 shows sample of FFT data obtained from the pressure sensor, on the top, and optical signal (on the bottom) when only one main oscillation mode was observed. The injector was operated at the same operating condition (T=31° C., fuel flow rate=39.7 lbs/hr. At the air flow rate of 0.256 lbs/sec, the excited acoustic modes were not steady—switching from one oscillation mode to two oscillation modes with different amplitudes. The optical sensor was able to measure both frequency and amplitude of oscillation at 1 Hz. Unfortunately, due to significant damping on the pressure probe, the absolute pressure amplitude was not obtained from the pressure sensor. The measurements verified that the pressure amplitudes for the measurement results shown in FIGS. 9 and 10 were less than 0.03 atm, by comparing the signal from the pressure probe with another pressure transducer located along the acoustic tube.

The following sections provide additional details on WMS based on optical sensing for real time measurements of equivalence ratio oscillations of a fuel and air in a gas combustion chamber. In the examples described below, the Wavelength Modulation Spectroscopy (WMS) is used to measure the second harmonic signal (2f signal) of a $CH_4$ absorption feature ($R_4$ manifold, $2v_3$ band) at 2 kHz. The amplitude and frequency of concentration fluctuations are determined from Fast Fourier Transformation (FFT) of the 2f signal at the center of the absorption feature. A mathematical model for the 2f signal of the R4 manifold, which consists of four strongly overlapped transitions, is used for quantification. The sensor is tested in a high-pressure acoustic flow cell, in which a $CH_4$ jet is actuated with a loudspeaker before mixing with an $N_2$ flow. Results illustrate real-time measurement of $CH_4$ concentration on the order of 5e-5 atm under high temperature and pressure conditions (T=644 K, $P_{tot}$=12.3 atm, equivalence ratio $\phi$=0.56, and optical path length L=7.6 cm).

It is desirable to operate gas turbines under stable conditions to increase the combustion efficiency and to control the undesired emission such as emission $NO_X$. Stationary gas turbines must be operated under extremely fuel-lean conditions in a way that minimizes the combustion instability.

Pressure perturbations brought on by instabilities can significantly shorten the combustor life time and may even cause catastrophic system damage. In addition, instabilities can degrade the combustion efficiency, resulting in increased emissions. There exists a need for a sensitive and robust sensor for measuring fuel/air oscillation. The present WMS sensing techniques can be designed to provide a non-intrusive optical sensor suitable for measuring the amplitude and frequency of equivalence ratio oscillations for high pressure/high temperature applications such as gas turbines.

The present optical sensor is based on tunable diode laser Wavelength Modulation Spectroscopy (WMS), in which the laser frequency is modulated by a sine wave while it is slowly tuned across an absorption feature by a ramp signal. When the laser beam passes through an absorbing media, the light is attenuated and this attenuation can be related to concentration of absorbing species using the Beer-Lambert law. When the absorbing species has a multiple overlapped absorption transitions, the in-phase component of the overall second harmonic signal (2f signal) at frequency $\bar{v}$ is related to concentration by $$I_{2f,p}(\bar{v}) = \qquad (1)$$
$$KK'I_0 \sum_{i=1}^{M} \int_{-\pi}^{+\pi} \frac{[1 + s_{F1}(\bar{v} - \bar{v}_0) + s_{F2}(\bar{v} - \bar{v}_0)^2 - s_f \Delta v_m \cos \omega t]}{\times \exp\{-\alpha_i[\bar{v} - \Delta v_m \cos(\omega t + \psi)]\} \cos(2wt + \theta) d\omega t},$$

where $\alpha(v)$ is absorbance and is calculated from $$\alpha_i = (v) = S_i(T)\phi_i(v - v_{0,i}) L P_{abs}. \qquad (2)$$

In Equations (1) and (2), K, K', and $I_0$ are photodetector gain, lock-in amplifier gain, and laser intensity at arbitrary frequency $\bar{v}_0$, respectively. Also, $s_{F1}$, $s_{F2}$ and $s_f$ are the laser intensity-frequency parameters, $\Delta v_m$ is the amplitude of frequency modulation, w is the angular frequency at modulation frequency $f(\omega=2\pi f)$, $\psi$ is the phase difference between frequency and intensity modulation of the diode laser, $\theta$ is the detection phase, L is optical path length and $P_{abs}$ is partial pressure of absorbing species, $S_i(T)$ is the line strength of transition i with absorption frequency of $v_{0,i}$ at temperature T, and $\phi_i$ is the line shape function of the transition i.

The WMS optical sensor can be used to measure the concentration of $CH_4$ based on absorption of the laser in the R4 manifold of $CH_4$ from a $2v_3$ band transition. To obtain the maximum response time, the laser frequency is modulated at the center of absorption feature at a frequency of 10 kHz (no sweep tuning is applied). Based on Eq. (1), for quantification of the 2f signal, laser parameters and spectroscopic properties of the selected $CH_4$ absorption feature including line strength and pressure broadening coefficients must be available. We measured the laser parameters experimentally for each operating condition and used the line strength and pressure broadening coefficients of the $CH_4$ transition. A C++ code was used for simulating the 2f signal based on Eq. (1), using the measured spectroscopic parameters.

Figure 11:
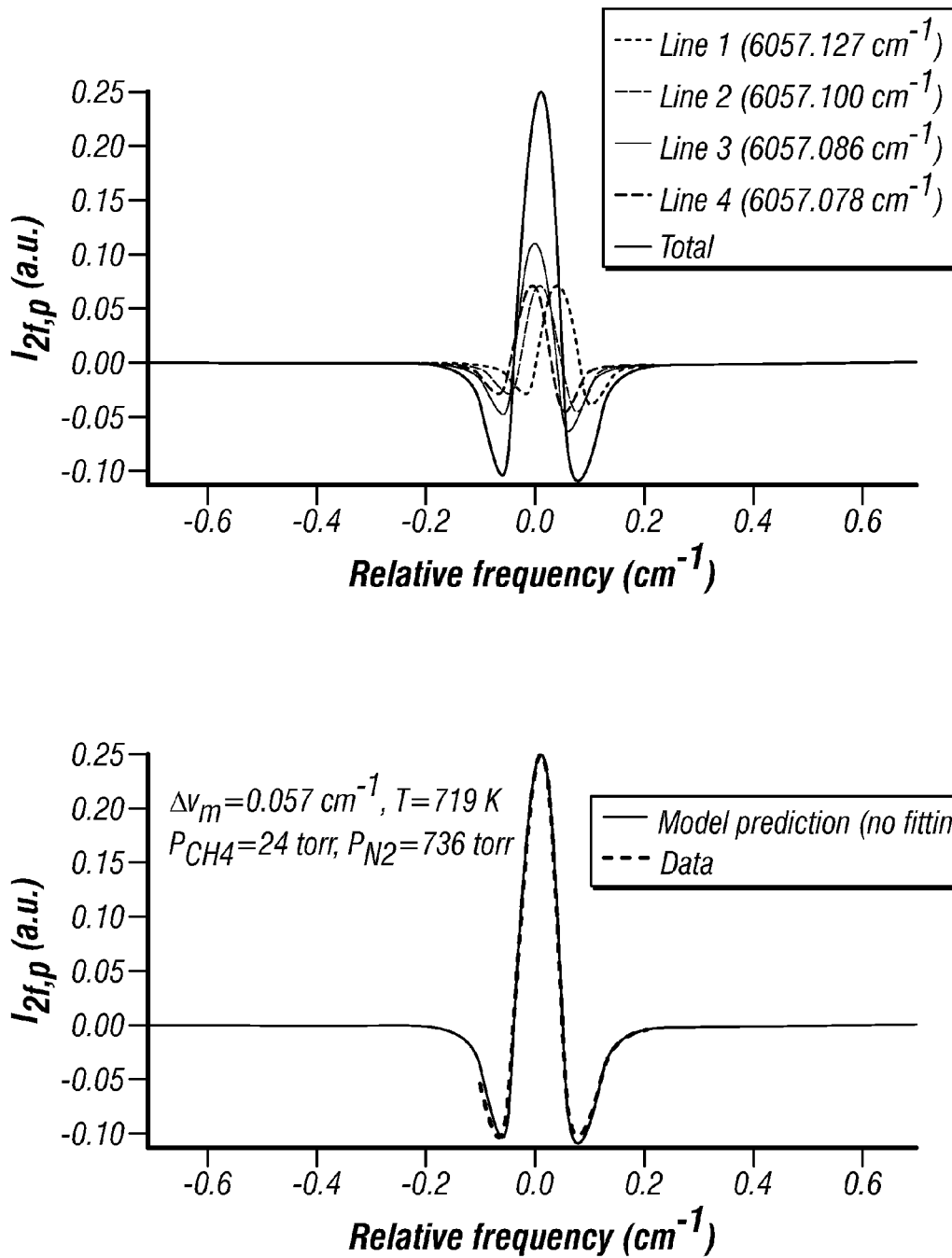
FIG. 11 shows a comparison between measured and simulated 2f spectra at atmospheric pressure.

FIG. 11 shows a comparison between measured and simulated 2f spectra at atmospheric pressure. The top trace shows the simulated 2f spectra of each individual transition and also overall 2f spectra (solid line). The bottom trace compares the overall simulated 2f spectra shown in top trace with measurement. The measured and simulated 2f spectra of the $CH_4$ transition are at a total pressure of 1 atm. and a pressure of 24 torr for $CH_4$. The temperature is 719 K. The measurement was performed in a temperature- and pressure-controlled 31.7-cm-long gas cell. As observed, the model can predict the 2f signal related to the four strongly-overlapped $CH_4$ transitions, accurately.

Figure 12:
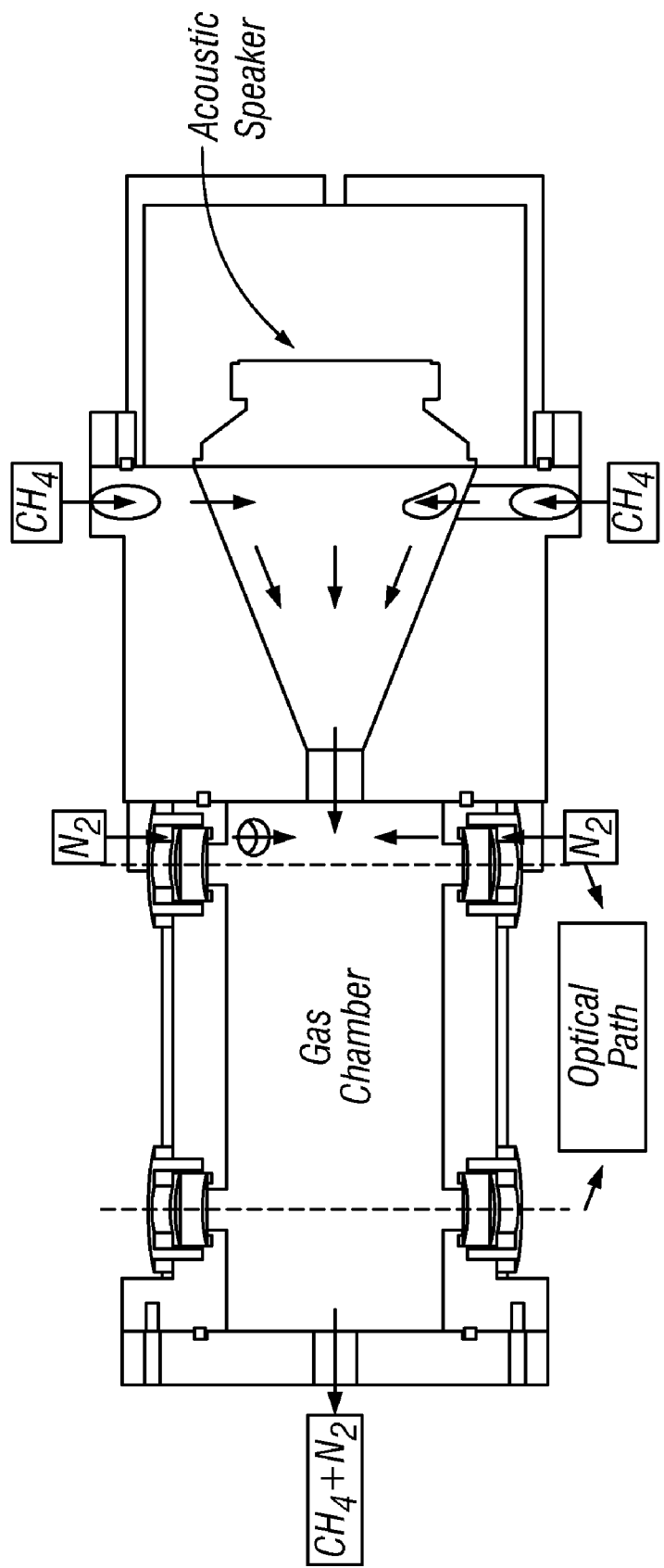
FIG. 12 shows a high pressure acoustic flow cell for testing the performance of the optical sensor in measuring the frequency and amplitude of CH4 concentration oscillations in a mixed flow of nitrogen and methane.

To test the performance of the optical sensor in measuring the frequency and amplitude of $CH_4$ concentration oscillation in a mixed flow of nitrogen and methane, a high pressure acoustic flow cell with optical path length of 7.6 cm was designed, built, and tested at different pressures. FIG. 12 shows the structure of this cell. In this cell, a high power (120-watt) speaker was driven with an oscillation signal from a function generator to create acoustic oscillations in the gas so that the $CH_4$ flow oscillates with the motion of the speaker diaphragm, proportionally to the applied voltage, without affecting the main $N_2$ flow. Based on the geometry of the acoustic cell, at certain frequencies the acoustic cell resonates and therefore provides a stronger oscillation in $CH_4$ flow rate. For safety considerations, we used a nitrogen flow instead of air to prevent any possible explosion of the fuel/air mixture. Once the acoustic cell was pressure tested, the optical sensor was mounted and applied to measure the fluctuation in the $CH_4/N_2$ ratio in the flow using the LabView™ program. Many experiments at different oscillation frequencies (100 Hz to 1 kHz) and pressures (1 to 11.2 atm) were performed. An example of the results of the measurement is shown in FIG. 3.

Figure 13:
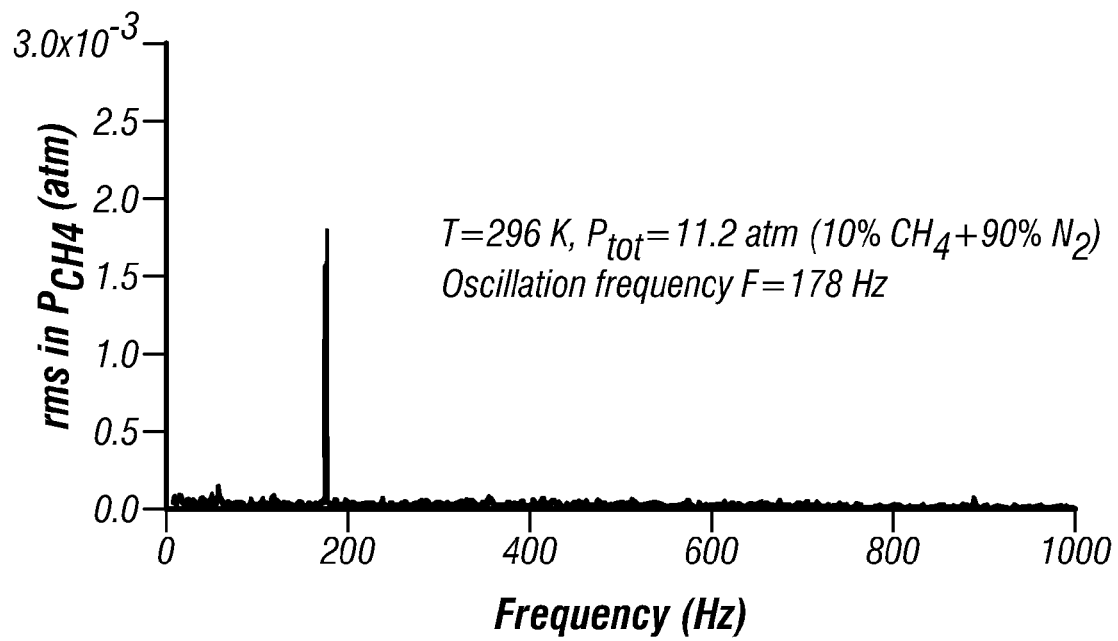
FIG. 13 shows measurements of the frequency and amplitude of the CH4 concentration (pressure) oscillation in CH4/N2 flow inside the acoustic system in FIG. 12 at room temperature and at two different pressures.
Figure 13:
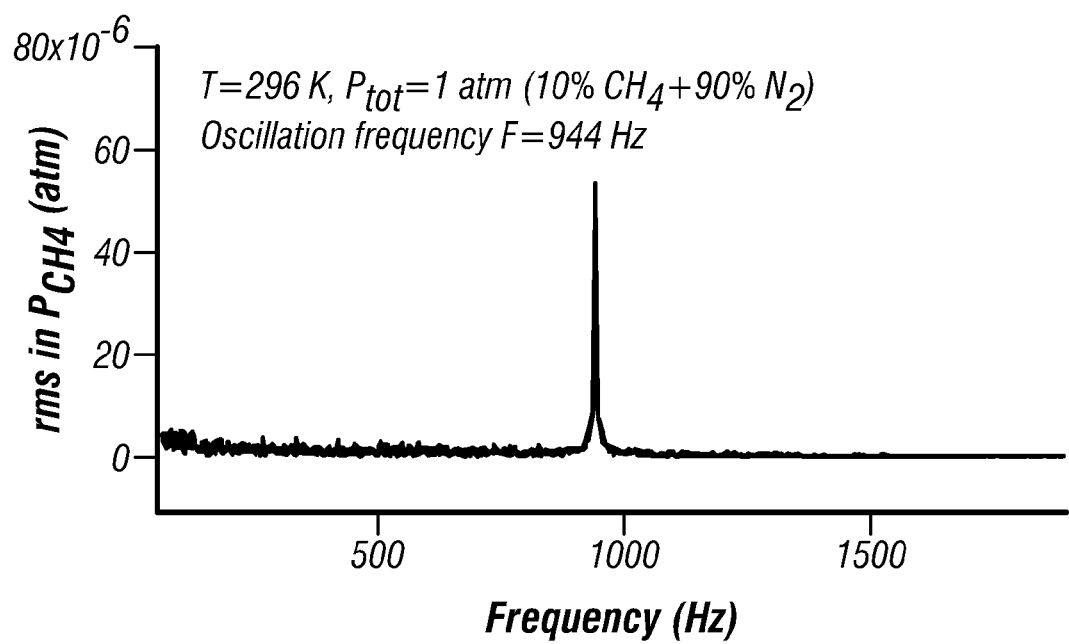

FIG. 13 shows measurements of the frequency and amplitude of the CH4 concentration (pressure) oscillation in CH4/N2 flow inside the acoustic system in FIG. 12 at the room temperature. Top and bottom traces show the measured FFT of 2f signal of CH4 when its flow rate was oscillated at 178 Hz and 944 Hz, respectively. Based on these results, we are able to observe $CH_4$ fluctuations on the order of 3e-6 and 2e-5 atm (with S/N=1) at system pressures of 1 and 11.2 atm, respectively, over the range of oscillation frequencies up to 1 kHz. In these experiments, for each system pressure, optimal modulation depths were chosen to maximize the 2f signal. From the room-temperature measurement results, the response of the sensor at high temperatures, and for systems with different mixture compositions, can be predicted through the simulation of the 2f signal.

Figure 14:
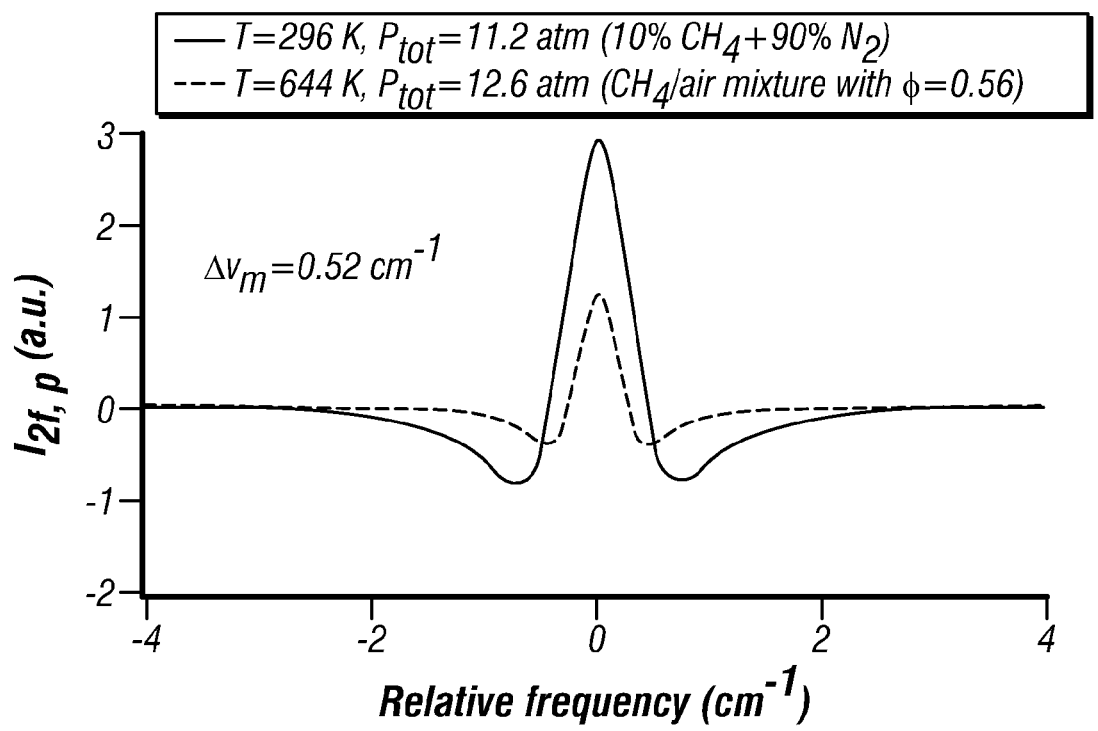
FIG. 14 shows comparison between the simulated 2f spectra of CH4/N2 mixture and CH4/air at different pressures, temperatures, and mixture compositions in the system in FIG. 12.

FIG. 14 shows simulated 2f spectra for a mixture of $CH_4/N_2$ at room temperature (similar to the high pressure measurement presented in FIG. 13) is compared to the 2f spectra of another mixture of $CH_4$/air at a higher temperature. From the results in FIG. 4 and also the oscillation measurement shown in FIG. 3, it can be predicted that the optical sensor could measure oscillations in $CH_4$ concentration on the order of 5e-5 atm at the lean, premixed gas-turbine type conditions specified in FIG. 14: T=644 K, $P_{tot}$=12.3 atm, equivalence ratio $\phi$=0.56, and optical path length L=7.6 cm.

While this specification contains many specifics, these should not be construed as limitations on the scope of any invention or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Only a few implementations and examples are described, variations and enhancements of the described implementations and examples, and other implementations are possible based on what is described. Other embodiments are within the scope of the following claims.

What is claimed is:

1. A method for optically sensing a gas medium based on Wavelength Modulation Spectroscopy, comprising:
modulating a laser wavelength of a tunable laser at a modulation frequency to produce a wavelength-modulated laser beam with a laser frequency range including an absorption band of molecules of a molecular species in the gas medium;
directing the wavelength-modulated laser beam that transmits through the gas medium;
measuring a transmission of the wavelength-modulated laser beam through the gas medium to obtain measurements of at least one signal at a harmonic frequency of the modulation frequency at different modulation depths in modulating the laser wavelength;
processing the measurements of the at least one signal at the harmonic frequency of the modulation frequency at different modulation depths to obtain a total broadening of absorption spectrum of the molecular species in the gas medium,
wherein the at least one signal comprises a first signal at a second harmonic frequency of the modulation frequency, and
wherein measuring the transmission of the wavelength-modulated laser beam through the gas medium comprises obtaining measurements of a second signal at a fourth harmonic frequency of the modulation frequency at different modulation depths in modulating the laser wavelength; and
processing the measurements of the second signal to obtain additional information on the gas medium.

2. The method as in claim 1, wherein the processing is performed without prior knowledge of a composition of the gas medium.

3. The method as in claim 1, wherein the processing is performed without prior knowledge of pressure broadening coefficients of the molecules of the molecular species of the gas medium.

4. The method as in claim 1, comprising:
using the signal at the second harmonic frequency to obtain a concentration of the molecules of the molecular species; and
using the second signal at the fourth harmonic frequency to obtain information on a pressure of the gas medium.

5. The method as in claim 1, comprising:
using the signal at the second harmonic frequency to obtain information on a pressure of the gas medium; and
using the second signal at the fourth harmonic frequency to obtain a concentration of the molecules of the molecular species.

6. A method for optically sensing a gas medium based on Wavelength Modulation Spectroscopy, comprising:
modulating a laser wavelength of a tunable laser at a modulation frequency to produce a wavelength-modulated laser beam with a laser frequency range including an absorption band of molecules of a molecular species in the gas medium;
directing the wavelength-modulated laser beam that transmits through the gas medium;
measuring a transmission of the wavelength-modulated laser beam through the gas medium to obtain measurements of at least one signal at a harmonic frequency of the modulation frequency at different modulation depths in modulating the laser wavelength;
processing the measurements of the at least one signal at the harmonic frequency of the modulation frequency at different modulation depths to obtain a total broadening of absorption spectrum of the molecular species in the gas medium;
in measuring the transmission of the wavelength-modulated laser beam through the gas medium, obtaining measurements of a second signal at a different harmonic frequency of the modulation frequency at different modulation depths in modulating the laser wavelength; and
processing the measurements of the second signal to obtain additional information on the gas medium.

7. A method for optically sensing a gas medium based on Wavelength Modulation Spectroscopy, comprising:
modulating a laser wavelength of a tunable laser at a modulation frequency to produce a wavelength-modulated laser beam with a laser frequency range including an absorption band of molecules of a molecular species in the gas medium;
directing the wavelength-modulated laser beam that transmits through the gas medium;
measuring a transmission of the wavelength-modulated laser beam through the gas medium to obtain measurements of at least one signal at a harmonic frequency of the modulation frequency at different modulation depths in modulating the laser wavelength;
processing the measurements of the at least one signal at the harmonic frequency of the modulation frequency at different modulation depths to obtain a total broadening of absorption spectrum of the molecular species in the gas medium;
modulating the laser wavelength of the tunable laser to make the at least one signal at the harmonic frequency to be sensitive to a concentration of the molecules of the molecular species;
modulating a laser wavelength of a second tunable laser at a second modulation frequency to produce a second wavelength-modulated laser beam with a laser frequency range including the absorption band of molecules of the molecular species in the gas medium;
directing the second wavelength-modulated laser beam through the gas medium;
measuring a transmission of the second wavelength-modulated laser beam through the gas medium to obtain measurements of a second signal at a harmonic frequency of the second modulation frequency at different modulation depths in modulating the laser wavelength;
modulating the laser wavelength of the second tunable laser to make the second signal at the harmonic frequency of the second modulation frequency to be sensitive to a pressure in the gas medium; and processing the at least one signal and the second signal to extract the concentration of the molecules of the molecular species and the pressure in the gas medium.

8. A method for optically sensing a gas medium based on Wavelength Modulation Spectroscopy, comprising:
modulating a laser wavelength of a tunable laser at a modulation frequency to produce a wavelength-modulated laser beam with a laser frequency range including an absorption band of molecules of a molecular species in the gas medium;
directing the wavelength-modulated laser beam that transmits through the gas medium;
measuring a transmission of the wavelength-modulated laser beam through the gas medium to obtain measurements of at least one signal at a harmonic frequency of the modulation frequency at different modulation depths in modulating the laser wavelength;
processing the measurements of the at least one signal at the harmonic frequency of the modulation frequency at different modulation depths to obtain a total broadening of absorption spectrum of the molecular species in the gas medium,
wherein the gas medium is a mixture of a gas fuel and air in a premixing gas chamber in a gas turbine or engine;
wherein the method comprises:
monitoring a pressure oscillation from the measured transmission of the wavelength-modulated laser beam; and
controlling injection of the gas fuel and air into the premixing gas chamber based on the monitored pressure oscillation to stabilize the pressure in the premixing gas chamber.

9. A method for performing Wavelength Modulation Spectroscopy measurements, comprising:
varying a modulation depth in modulating a laser wavelength of a laser used in the Wavelength Modulation Spectroscopy for measuring a gas medium to obtain measurements;
obtaining a total pressure broadening from the obtained measurements without prior knowledge of individual pressure broadening coefficients and gas composition;
operating a second laser used in the Wavelength Modulation Spectroscopy with a different modulation depth and a different modulation frequency from operating the laser;
detecting optical transmissions of the two laser beams through the gas medium from the laser and the second laser, respectively;
extracting a first second harmonic signal from detected optical transmission of the laser beam from the laser;
extracting a second harmonic signal from detected optical transmission of another laser beam from the second laser; and
processing the first and the second harmonic signals to obtain the total pressure broadening and a concentration of a fuel in the gas medium.

10. A method for performing Wavelength Modulation Spectroscopy measurements, comprising:
varying a modulation depth in modulating a laser wavelength of a laser used in the Wavelength Modulation Spectroscopy for measuring a gas medium to obtain measurements;
obtaining a total pressure broadening from the obtained measurements without prior knowledge of individual pressure broadening coefficients and gas composition, wherein the gas medium is a mixture of a gas fuel and air in a premixing gas chamber in a gas turbine;
monitoring a pressure oscillation from a transmission of the wavelength-modulated laser beam that passes through the gas medium; and
controlling injection of the gas fuel and air into the premixing gas chamber based on the monitored pressure oscillation to stabilize the pressure in the premixing gas chamber.

11. A method for optically measuring a gas medium based on Wavelength Modulation Spectroscopy, comprising:
directing a laser beam from a wavelength-modulated tunable diode laser through the gas medium;
measuring two different harmonic signals which have different responses to a total pressure in the gas medium to obtain both a gas concentration and a total pressure in the gas medium; wherein the gas medium is a mixture of a gas fuel and air in a premixing gas chamber in a gas turbine or engine;
monitoring a pressure oscillation from the measured transmission of the wavelength-modulated laser beam; and
controlling injection of the gas fuel and air into the premixing gas chamber based on the monitored pressure oscillation to stabilize the pressure in the premixing gas chamber.

12. The method as in claim 11, wherein:
the two different harmonic signals are at a first frequency which is a second harmonic of a modulation frequency in modulating the wavelength-modulated tunable diode laser and a second frequency which is a fourth harmonic of the modulation frequency.

13. A method for optically measuring a gas medium based on Wavelength Modulation Spectroscopy, comprising:
directing a first laser beam from a first wavelength-modulated tunable diode laser through the gas medium and a second laser beam from a second wavelength-modulated tunable diode laser through the gas medium, wherein the first wavelength-modulated tunable diode laser and the second wavelength-modulated tunable diode laser are modulated at respective modulation frequencies;
operating the first and the second tunable diode lasers differently with respect to a respective optimum modulation depth; and
measuring a harmonic signal of the modulation frequency from the first laser beam and a second harmonic signal at a harmonic frequency of the second laser beam to obtain both a gas concentration and a total pressure in the gas medium.

14. The method as in claim 13, wherein the harmonic signal from the first laser beam is at a frequency equal to a second harmonic of the modulation frequency in the first laser beam and the second harmonic signal from of the second laser beam is at a frequency equal to a second harmonic of the modulation frequency in the second laser beam.

15. The method as in claim 13, wherein the gas medium is a mixture of a gas fuel and air in a premixing gas chamber in a gas turbine, and
wherein the method comprises:
monitoring a pressure oscillation from the measured transmission of the first and second laser beams; and
controlling injection of the gas fuel and air into the premixing gas chamber based on the monitored pressure oscillation to stabilize the pressure in the premixing gas chamber.

16. A gas turbine system, comprising:
a gas turbine having a premixing gas chamber;
a first input port to input air into the premixing gas chamber;

a second input port to input a gas fuel into the premixing gas chamber to mix with the air;

a wavelength modulation spectroscopy (WMS) optical monitoring device having at least one tunable laser to produce a wavelength-modulated laser beam and to direct the laser beam through at least a portion within the premixing gas chamber to interact with a mixture of the gas fuel and the air; and an optical detector to receive an optical transmission of the laser beam;

a WMS processing device that processes an output of the optical detector to extract at least one signal at a harmonic frequency of the modulation frequency at different modulation depths; and a turbine control mechanism in communication with the WMS processing device and operable to control the gas fuel and the air input into the premixing gas chamber based on information in the at least one signal at the harmonic frequency of the modulation frequency.

17. The system as in claim 16, wherein the WMS optical monitoring device comprises two different tunable lasers to produce two wavelength-modulated laser beams and two optical detectors that respectively receive optical transmission signals of the two laser beams through the premixing gas chamber.

* * * * *